(12) United States Patent
Liu et al.

(10) Patent No.: US 10,194,887 B2
(45) Date of Patent: Feb. 5, 2019

(54) DISPLAY DEVICE FOR ULTRASOUND ENERGY

(71) Applicant: CHANG GUNG UNIVERSITY, Tao-Yuan (TW)

(72) Inventors: Hao-Li Liu, Tao-Yuan (TW); Jing-Jing Xia, Tao-Yuan (TW)

(73) Assignee: CHANG CHUNG UNIVERSITY, Tao-Yuan (TW)

( * ) Notice: Subject to any disclaimer, the term of this patent is extended or adjusted under 35 U.S.C. 154(b) by 293 days.

(21) Appl. No.: 15/204,456

(22) Filed: Jul. 7, 2016

(65) Prior Publication Data

US 2017/0035391 A1    Feb. 9, 2017

(30) Foreign Application Priority Data

Aug. 3, 2015   (CN) .......................... 2015 1 0467721

(51) Int. Cl.
*A61B 8/00* (2006.01)
*A61N 7/00* (2006.01)
*A61N 7/02* (2006.01)
*A61B 8/08* (2006.01)

(52) U.S. Cl.
CPC .......... *A61B 8/463* (2013.01); *A61B 8/0808* (2013.01); *A61N 7/00* (2013.01); *A61N 7/02* (2013.01); *A61B 8/0891* (2013.01); *A61B 8/4494* (2013.01); *A61B 8/5207* (2013.01); *A61N 2007/0052* (2013.01); *A61N 2007/0095* (2013.01)

(58) Field of Classification Search
CPC ............................. A61B 8/463; A61B 4/0808
See application file for complete search history.

(56) References Cited

U.S. PATENT DOCUMENTS

| | | | |
|---|---|---|---|
| 2008/0114248 A1* | 5/2008 | Urbano | A61B 8/4472 600/447 |
| 2011/0213254 A1* | 9/2011 | Ting | A61B 5/02007 600/485 |
| 2015/0182195 A1* | 7/2015 | Liu | A61B 8/4494 600/459 |

* cited by examiner

*Primary Examiner* — Joel F Brutus
(74) *Attorney, Agent, or Firm* — Muncy, Geissler, Olds & Lowe, P.C.

(57) ABSTRACT

A display device for ultrasound energy includes a focused ultrasound emitting and receiving device, a processing device and a display. The processing device generates a first electrical signal and transmits it to the focused ultrasound emitting and receiving device to control the focused ultrasound emitting and receiving device to emit at least one first ultrasound signal to a target position of an organism. The target position reflects the first ultrasound signal to form at least one second ultrasound signal. After generating the first electrical signal, the processing device drives the focused ultrasound emitting and receiving device to start to receive the second ultrasound signal only during a preset period after the estimation period. The processing device uses the display to display an image of the target position according to the second ultrasound signal, and brightness of the image is directly proportional to energy intensity of the first ultrasound signal.

18 Claims, 7 Drawing Sheets

DISPLAY DEVICE FOR ULTRASOUND ENERGY

This application claims priority for China patent application no. 201510467721.8 filed on Aug. 3, 2015, the content of which is incorporated by reference in its entirely.

BACKGROUND OF THE INVENTION

Field of the Invention

The present invention relates to a display device, particularly to a display device for ultrasound energy.

Description of the Related Art

The conventional focusing-type ultrasonic apparatus can generate focused function by selecting suitable frequency range of 200 kHz to 2 MHz. Meantime, the focused area has sufficient high acoustic pressure so that capable of inducing localized blood-brain barrier (BBB) disruption, which is an important implication on noninvasively delivering drug into brain. Although the conventional focusing-type ultrasonic apparatus can induce localized blood-brain barrier (BBB) disruption temporarily, yet they are still high-frequency ultrasonic systems. Thus the invasive way has to be used to induce BBB disruption, and it still is concentrated to a small area. It is unable to reach the work of inducing larger area of BBB disruption. Also, the cost of system is pretty high and there are no more extensive applications.

Although the high-frequency ultrasonic system is easier to focus energy to the focal point, most energy is easy to be absorbed by hard tissues such as skull etc, thus the ultrasonic effect will be reduced. It can only be operated after the animal skull being removed; thus the high-frequency ultrasonic system is still an invasive drug release brain therapy system. Due to ultrasonic energy can only focus to a single focal point, it is unable to induce larger area of BBB disruption effectively. If one wants the apparatus to open BBB without removing the skull, then the ultrasound energy cannot be too low. However, too much ultrasound energy can directly damage capillary rather than opening the tight junctions. There are some technologies such as acoustic radiation force imaging that applies a sufficiently high and continuous-wave mode ultrasound to detect acoustic patterns; however, the receiving time of the technology is too long so that the distribution of signals is hard to be identified. Besides, since the excessive ultrasound energy required by this technology typically induces thermally and mechanically damages organism tissue, the purpose of using such technology to monitor the blood-to-brain permeability is not practical. To overcome the abovementioned problems, the present invention provides a display device for ultrasound energy, so as to solve the afore-mentioned problems of the prior art.

SUMMARY OF THE INVENTION

A primary objective of the present invention is to provide a display device for ultrasound energy, which controls a focused ultrasound emitting and receiving device to emit an ultrasound signal to an organism and, after an estimation period, receive the backscattering ultrasound signal, thereby generating an image of the organism. Wherein, brightness of the image is directly proportional to energy intensity of the ultrasound signal. This invention can be applied for monitoring the induction of BBB opening and drug delivery.

To achieve the abovementioned objectives, the present invention provides a display device for ultrasound energy, which comprises a focused ultrasound emitting and receiving device, a processing device and a display. The focused ultrasound emitting and receiving device emits at least one first ultrasound signal to a target position of an organism, and the target position reflects the first ultrasound signal to form at least one second ultrasound signal. The processing device is connected with the focused ultrasound emitting and receiving device and sets an estimation period according to a distance between the focused ultrasound emitting and receiving device and the target position as well as a given sound traveling speed. The processing device generates a first electrical signal and transmits the first electrical signal to the focused ultrasound emitting and receiving device to control the focused ultrasound emitting and receiving device to emit the first ultrasound signal, and then the processing device drives the focused ultrasound emitting and receiving device to start to receive the second ultrasound signal only during a preset period after the estimation period. The preset period is equal to or larger than response time of the focused ultrasound emitting and receiving device. The display is connected with the processing device. The processing device display a first image of the target position according to the second ultrasound signal, and brightness of the first image is directly proportional to energy intensity of the first ultrasound signal.

Below, the embodiments are described in detail in cooperation with the drawings to make easily understood the technical contents, characteristics and accomplishments of the present invention.

BRIEF DESCRIPTION OF THE DRAWINGS

FIG. 7(*a*) is a diagram showing an image of blood-brain barrier (BBB) opened effect observed from stained brain tissues under sound pressure of 0.467 MPa according to an embodiment of the present invention;

FIG. 7(*b*) is a diagram showing a second image corresponding to FIG. 7(*a*);

FIG. 8(*a*) is a diagram showing an image of blood-brain barrier (BBB) opened effect observed from stained brain tissues under sound pressure of 0.705 MPa according to an embodiment of the present invention;

FIG. 8(*b*) is a diagram showing a second image corresponding to FIG. 8(*a*)

DETAILED DESCRIPTION OF THE INVENTION

Figure 1:
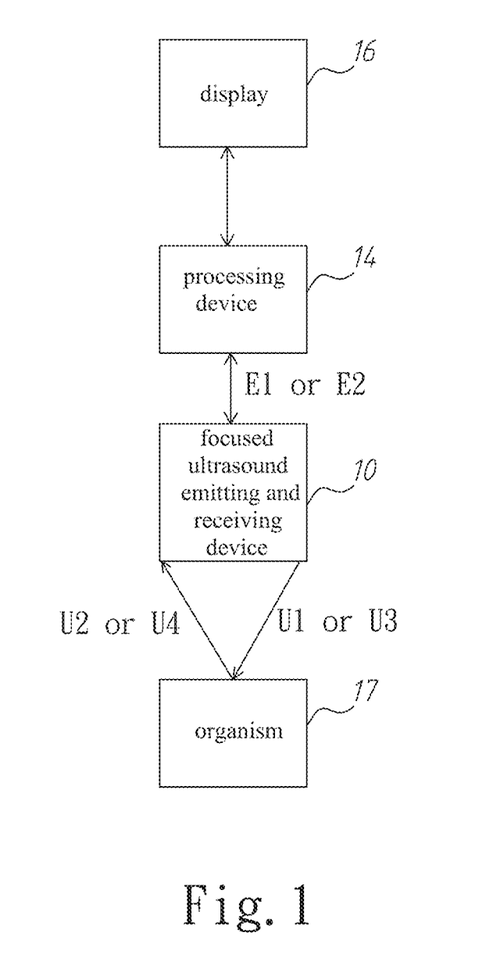
FIG. 1 is a block diagram showing a device according to an embodiment of the present invention.
Figure 2:
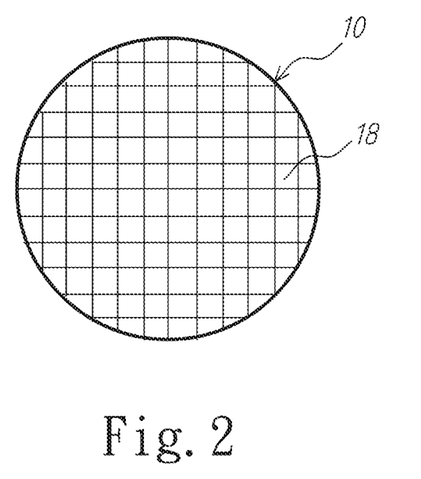
FIG. 2 is a diagram schematically showing focused ultrasound transducers arranged into a two-dimensional array according to an embodiment of the present invention.
Figure 3:
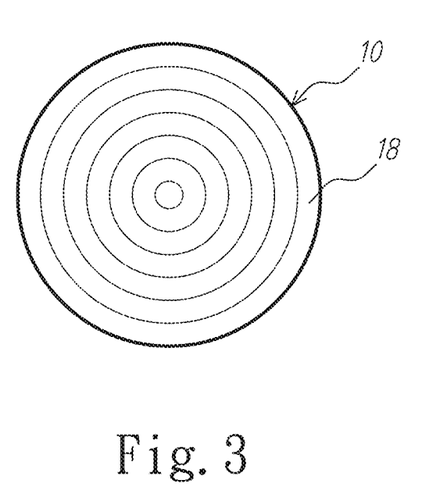
FIG. 3 is a diagram schematically showing focused ultrasound transducers arranged into a concentric circle array according to an embodiment of the present invention.

Below is the first embodiment of the present invention. Refer to FIG. 1, FIG. 2 and FIG. 3. The present invention comprises a focused ultrasound emitting and receiving device 10, a processing device 14 and a display 16. The processing device 14 is connected with the focused ultrasound emitting and receiving device 10 and the display 16. The position of the focused ultrasound emitting and receiving device 10 corresponds to a target position of an organism 17. For example, the organism 17 is a central nervous system (CNS) tissue with the microvascular structure containing blood-brain barrier (BBB) for each CNS capillary. The focused ultrasound emitting and receiving device 10 further comprises at least one focused ultrasound transducer 18 or a plurality of focused ultrasound transducers 18. In the first embodiment, the focused ultrasound emitting and receiving device 10 comprises a plurality of focused ultrasound transducers 18 arranged into a two-dimensional square-diced array or a concentric ring-shape array on a curved surface, wherein the two-dimensional square-diced array or a concentric ring-shape array are respectively shown in FIG. 2 and FIG. 3.

According to a distance between the ultrasound transducer 18 and the target position and sound-traveling speed, the processing device 14 sets an estimation period. For example, there is a distance between the target position and the focused ultrasound transducer 18 farthest from the target position, and the estimation period equals the distance multiplied by 2 and divided by the sound-traveling speed. The processing device 14 generates a first electrical signal E1 and transmits the first electrical signal E1 to the focused ultrasound transducers 18 to control the focused ultrasound transducers 18 to emit at least one first ultrasound signal U1 to the target position. The first ultrasound signal U1 penetrates through cranial bone to reach the target position. The target position reflects the first ultrasound signal U1 to form at least one second ultrasound signal U2. In the first embodiment, there are a plurality of first ultrasound signals U1 and a plurality of second ultrasound signals U2. After generating the first electrical signal E1, the processing device 14 drives the focused ultrasound transducers 18 to start to receive the second ultrasound signals U2 penetrating through the cranial bone only during a preset period after the estimation period. The processing device 14 drives the focused ultrasound transducers 18 to stop receiving any ultrasound signals during the other period. The preset period is equal to or larger than response time of the focused ultrasound transducer 18. The processing device 14 uses the display 16 to display a first image of the target position according to the second ultrasound signals U2. Since energy intensity of the first ultrasound signals U1 is directly proportional to energy intensity of the second ultrasound signals U2 and brightness of the first image is directly proportional to the energy intensity of the second ultrasound signals U2, the brightness of the first image is directly proportional to the energy intensity of the first ultrasound signals U1. The processing device 14 converts the first electrical signal E1 into a second electrical signal E2 received by the focused ultrasound transducers 18 according to a difference between the brightness of the first image and preset brightness. The focused ultrasound transducers 18 use the second electrical signal E2 to emit at least one third ultrasound signal U3 whose energy intensity larger than energy intensity of the first ultrasound signal U1 to the target position. The third ultrasound signal U3 penetrates through the cranial bone to reach the target position. The target position reflects the third ultrasound signal U3 to form at least one fourth ultrasound signal U4. In the first embodiment, there are a plurality of third ultrasound signals U3 and a plurality of fourth ultrasound signals U4. After generating the third ultrasound signals U3, the processing device 14 drives the focused ultrasound transducers 18 to start to receive the fourth ultrasound signals U4 through the cranial bone only during the preset period after the estimation period. The processing device 14 drives the focused ultrasound transducers 18 to stop receiving any ultrasound signals during the other period. The first ultrasound signals U1, the second ultrasound signals U2, the third ultrasound signals U3 and the fourth ultrasound signals U4 are burst-tone waves. The higher the frequency of the first ultrasound signals U1, the second ultrasound signals U2, the third ultrasound signals U3 and the fourth ultrasound signals U4 is, the thinner the thickness of the cranial bone penetrated are. In other words, the frequency of the first ultrasound signal U1, the second ultrasound signal U2, the third ultrasound signal U3 and the fourth ultrasound signal U4 is inversely proportional to the thickness of the cranial bone penetrated. The processing device 14 uses the display 16 to display a second image of the target position according to the fourth ultrasound signals U4. Since energy intensity of the third ultrasound signals U3 is directly proportional to energy intensity of the fourth ultrasound signals U4 and brightness of the second image is directly proportional to the energy intensity of the fourth ultrasound signals U4, the brightness of the second image is directly proportional to the energy intensity of the third ultrasound signals U3.

Below is the operation process of the first embodiment. Refer to FIG. 1, FIG. 2, FIG. 3 and FIG. 4. Firstly, a calibration process is performed. The calibration process comprises Step S10, Step S12 and Step S14. In the beginning, Step S10 is performed. In Step S10, the processing device 14 generates the first electrical signal E1 and transmits the first electrical signal E1 to the focused ultrasound transducers 18 to control the focused ultrasound transducers 18 to emit the first ultrasound signals U1 to the target position. Then, in Step S12, the first ultrasound signals U1 penetrate through the cranial bone to reach the target position and the target position reflects the first ultrasound signals U1 from the focal position and backscatters them to ultrasound transducer 18 to form the second ultrasound signals U2 in the estimation period. The processing device 14 drives the focused ultrasound transducers 18 to start to receive the second ultrasound signals U2 through the cranial bone only during the preset period after the estimation period. Then, in Step S14, the processing device 14 uses the display 16 to display the first image of the target position according to the second ultrasound signals U2, whereby the brightness of the first image is directly proportional to the energy intensity of the first ultrasound signals U1.

The first image is displayed according to first beamformed filtered data $\tilde{rf}(x_g, y_g, z_g)$, and the first beamformed filtered data $\tilde{rf}(x_g, y_g, z_g)$ satisfies following formulas (1), (2), (3), (4) and (5):

$$\tilde{rf}(x_g, y_g, z_g) = F \otimes \sum_{n=1}^{N} \left( \sum_{n=1}^{N} \left( (\hat{RF}_{M \times N})^T \times x_{M \times 1} \times \overline{TD_{1 \times N}} \right) \right) \quad (1)$$

$$\hat{RF}_{M \times N} \cong \cos(2\pi f_r t) \times (ch\hat{RF}_{M \times N} + ch\hat{RF}^*_{M \times N})/2 - \sin(2\pi f_r t) \times (-j) \times (ch\hat{RF}_{M \times N} + ch\hat{RF}^*_{M \times N})/2 \quad (2)$$

-continued $$\hat{IQ}_{m \times N} \cong [f_1(k), f_2(k), \ldots, f_i(k), \ldots, f_N(k)] \quad (3)$$

$$ch\hat{RF}_{M \times N} \cong \left[ f_1\left(\frac{k}{f_{sIQ}} * f_{sRF}\right), f_2\left(\frac{k}{f_{sIQ}} * f_{sRF}\right), \ldots, \right. \quad (4)$$
$$\left. f_i\left(\frac{k}{f_{sIQ}} * f_{sRF}\right), \ldots, f_N\left(\frac{k}{f_{sIQ}} * f_{sRF}\right) \right]$$

$$T_{M \times N} = x_{M \times 1} \times \overline{TD_{1 \times N}} \quad (5)$$

Wherein, ($x_g$, $y_g$, $z_g$) is 3-D coordinate of the target position, and F is a first filtered factor, and N is an amount of the focused ultrasound transducer 18, and n is an index of each focused ultrasound transducer 18, and $\hat{RF}_{M \times N}$ is a first beamformed data matrix with dimension M×N, and t is time, and $f_r$ is a first re-modulation frequency, and $ch\hat{RF}_{M \times N}$ is a first channel data matrix with dimension M×N, and $\hat{IQ}_{m \times N}$ is a matrix with dimension m×N of a baseband signal of the second ultrasound signal U2, and in is a natural number, and $f_i(k)$ is a column function of a i-th column of $\hat{IQ}_{m \times N}$, and k and i are natural numbers, and k=1,2, . . . , m, and i=1, 2, . . . , N, and $f_{sIQ}$ is a sampling frequency of $\hat{IQ}_{m \times N}$, and $f_{sRF}$ is a resampled frequency of $\hat{IQ}_{m \times N}$, and $\overline{TD_{1 \times N}}$ is a first time backscattered data matrix of the second ultrasound signal U2 moving from the target position to N pieces of the focused ultrasound transducers, and $T_{M \times N}$ is a mask-operated matrix with dimension M×N comprising binary element 0 or 1, and M is a natural number larger than the largest element of the first time matrix, and $x_{M \times 1}$ is a vector with dimension M×1, and $ch\hat{RF}_{M \times N}{}^*$ is a conjugation of $ch\hat{RF}_{M \times N}$, and ⊗ is convolution operation.

The energy intensity of the first ultrasound signals U1 is relatively low in ultrasound energy level. An excessive energy intensity of the first ultrasound signals U1 can damage the organism 17. As a result, the low energy intensity of the first ultrasound signals U1 applies to the organism 17, so as to know how much energy applied to the organism 17 and how much energy absorbed by the cranial bone. The processing device 14 knows how much energy applied to the organism 17 according to the brightness of the first image. The higher the brightness of the first image is, the stronger the energy applied to the target position of the organism 17 is. The processing device 14 of the present invention sets the preset brightness as an energy level intended to apply to the target position of the organism 17.

Figure 4:
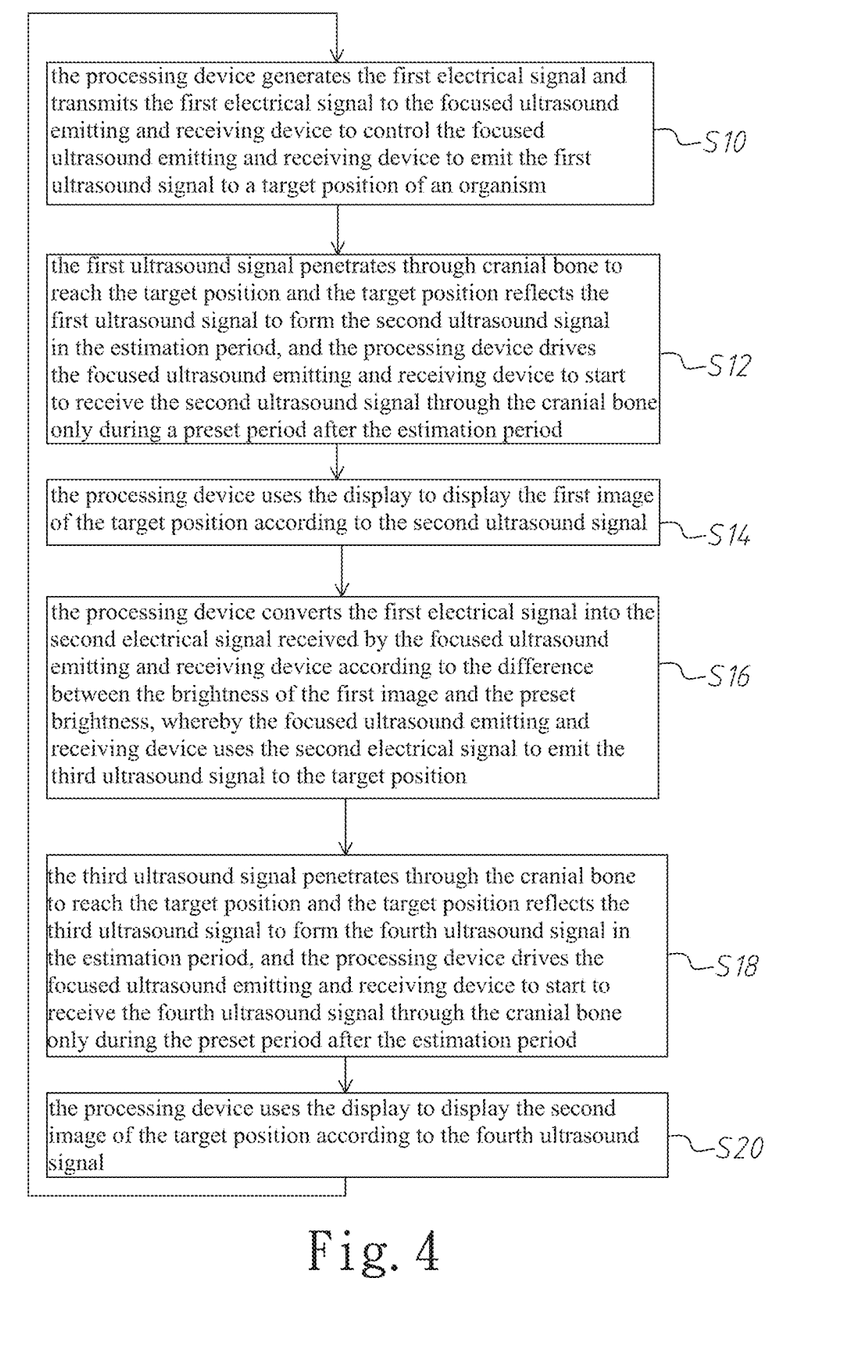
FIG. 4 is a flowchart diagram showing operation of the device according to an embodiment of the present invention.

After the calibration process, an execution process is performed. The execution process comprises Step S16, Step S18 and Step S20. In the execution process, Step S16 is firstly performed. In Step S16, the processing device 14 converts the first electrical signal E1 into the second electrical signal E2 received by the focused ultrasound transducers 18 according to the difference between the brightness of the first image and the preset brightness, whereby the focused ultrasound transducers 18 use the second electrical signal E2 to emit the third ultrasound signals U3 whose energy intensity larger than the energy intensity of the first ultrasound signals U1 to the target position. Then, in Step S18, the third ultrasound signals U3 penetrate through the cranial bone to reach the target position and the target position reflects the third ultrasound signals U3 to form the fourth ultrasound signals U4 in the estimation period. The processing device 14 drives the focused ultrasound transducers 18 to start to receive the fourth ultrasound signals U4 through the cranial bone only during the preset period after the estimation period. Then, in Step S20, the processing device 14 uses the display 16 to display the second image of the target position according to the fourth ultrasound signals U4, whereby the brightness of the second image is directly proportional to the energy intensity of the third ultrasound signals U3.

The second image is displayed according to second beamformed filtered data $\tilde{rf}(x_g, y_g, z_g)'$, and the second beamformed filtered data $\tilde{rf}(x_g, y_g, z_g)'$ satisfies following formulas (6), (7), (8), (9) and (10):

$$\tilde{rf}(x_g, y_g, z_g)' = F' \otimes \sum_{n=1}^{N} \left( \sum_{n=1}^{N} \left( (\hat{RF}'_{M' \times N})^T \times x'_{M' \times 1} \times \overline{TD'_{1 \times N}} \right) \right) \quad (6)$$

$$\hat{RF}'_{M \times N} \cong \cos(2\pi f'_r t) \times \left( ch\hat{RF}'_{M' \times N} + ch\hat{RF}'^*_{M' \times N} \right)/2 - \quad (7)$$
$$\sin(2\pi f'_r t) \times (-j) \times \left( ch\hat{RF}'_{M' \times N} + ch\hat{RF}'^*_{M' \times N} \right)/2$$

$$\hat{IQ}'_{m' \times N} \cong [f'_1(k), f'_2(k), \ldots, f'_i(k), \ldots, f'_N(k)] \quad (8)$$

$$ch\hat{RF}'_{M' \times N} \cong \left[ f'_1\left(\frac{k}{f'_{sIQ}} * f'_{sRF}\right), f'_2\left(\frac{k}{f'_{sIQ}} * f'_{sRF}\right), \ldots, \right. \quad (9)$$
$$\left. f'_i\left(\frac{k}{f'_{sIQ}} * f'_{sRF}\right), \ldots, f'_N\left(\frac{k}{f'_{sIQ}} * f'_{sRF}\right) \right]$$

$$T'_{M' \times N} = x'_{M' \times 1} \times \overline{TD'_{1 \times N}} \quad (10)$$

Wherein, ($x_g$, $y_g$, $z_g$) is 3-D coordinate of the target position, and F' is a second filtered factor, and N is an amount of the focused ultrasound transducer 18, and n is an index of each focused ultrasound transducer 18, and $\hat{RF}'_{M' \times N}$ is a second beamformed data matrix with dimension M'×N, and t is time, and $f_r'$ is a second re-modulation frequency, and $ch\hat{RF}'_{M' \times N}$ is a second channel data matrix with dimension M'×N, and $\hat{IQ}'_{m \times N}$ is a matrix with dimension m×N of a baseband signal of the fourth ultrasound signal U4, and m is a natural number, and $f_i'(k)$ is a column function of a i-th column of $\hat{IQ}'_{m \times N}$, and k and i are natural numbers, and k=1,2, . . . , m, and i=1,2, . . . , N, and $f_{sIQ}'$ is a sampling frequency of $\hat{IQ}'_{m \times N}$, and $f_{sRF}'$ is a resampled frequency of $\hat{IQ}'_{m \times N}$, and $\overline{TD'_{1 \times N}}$ is a second time matrix of the fourth ultrasound signal U4 moving from the target position to N pieces of the focused ultrasound transducers 18, and $T'_{M' \times N}$ is a mask-operated matrix with dimension M'×N comprising binary element 0 or 1, and M' is a natural number larger than the largest element of the second time matrix, and $x'_{M' \times 1}$ is a vector with dimension M'×1, $ch\hat{RF}'_{M' \times N}{}^*$ is a conjugation of $ch\hat{RF}'_{M' \times N}$, and ⊗ is convolution operation.

After Step S20, the operation process returns to Step S10 to sequentially perform the calibration process and the execution process on another target position. Repeatedly, an activity of applying energy to a therapy region in CNS tissue is completed to achieve the purpose of opening the BBB and delivering drugs.

Besides, before the calibration process, the processing device 14 generates an electrical signal and transmits the electrical signal to the focused ultrasound transducers 18 to control the focused ultrasound transducers 18 to emit ultrasound signals to a calibrated tool such as a force balanced meter or a calibrated hydrophone for acoustic power measurement, whereby the correlation between level of ultrasound signal and the level of emitted energy can be established after performing the calibrate process.

Figure 5:
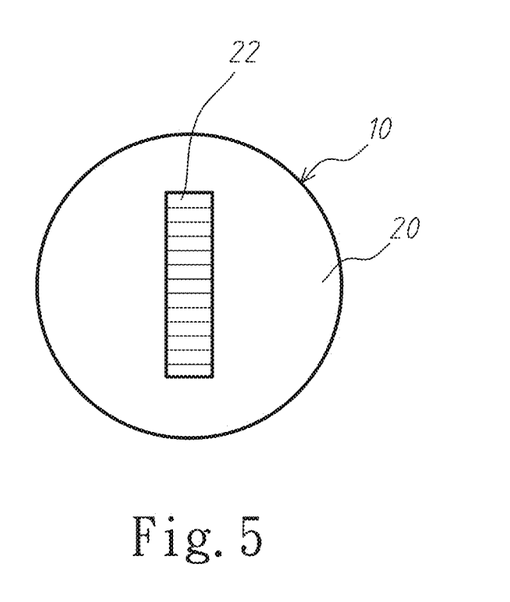
FIG. 5 is a diagram schematically showing a focused ultrasound emitting and receiving device formed by a plurality of ultrasound emitters and an ultrasound receiver according to an embodiment of the present invention.
Figure 6:
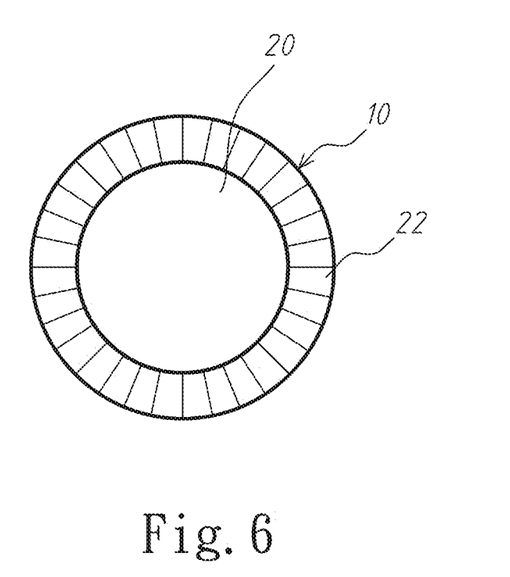
FIG. 6 is a diagram schematically showing a focused ultrasound emitting and receiving device formed by an ultrasound emitter and a plurality of ultrasound receivers according to an embodiment of the present invention.

Below is the second embodiment of the present invention. Refer to FIG. 1, FIG. 5 and FIG. 6. The second embodiment is different from the first embodiment in internal elements of the focused ultrasound emitting and receiving device 10. In the second embodiment, the focused ultrasound emitting and receiving device 10 further comprises at least one focused ultrasound emitter 20 and at least one focused ultrasound receiver 22 connected with the processing device 14. In one embodiment, the focused ultrasound emitter 20 is surrounded by the focused ultrasound receiver 22, or vice versa. The preset period is equal to or larger than response time of the focused ultrasound receiver 22. There is a distance between the target position and the focused ultrasound receiver 22 farthest from the target position. The estimation period equals the distance multiplied by 2 and divided by sound-traveling speed. In the second embodiment, there is a plurality of focused ultrasound receivers 22 arranged into a strip array with one dimension, and one focused ultrasound emitter 20. The focused ultrasound emitter 20 and the focused ultrasound receivers 22 are arranged on a curved surface, as shown in FIG. 5. In this case, there are one first ultrasound signal U1, one second ultrasound signal U2, one third ultrasound signal U3 and one fourth ultrasound signal U4. Alternatively, an amount of the focused ultrasound emitter 20 is one, and there is a plurality of focused ultrasound receivers 22. The focused ultrasound emitter 20 and the focused ultrasound receivers 22 are arranged into a ring array on a curved surface, as shown in FIG. 6. In this case, there are one first ultrasound signal U1, one second ultrasound signal U2, one third ultrasound signal U3 and one fourth ultrasound signal U4.

Below is the operation process of the second embodiment. Refer to FIG. 1, FIG. 4, FIG. 5 and FIG. 6. Firstly, a calibration process is performed. The calibration process comprises Step S10, Step S12 and Step S14. In the beginning, Step S10 is performed. In Step S10, the processing device 14 generates the first electrical signal E1 and transmits the first electrical signal E1 to the focused ultrasound emitter 20 to control the focused ultrasound emitter 20 to emit the first ultrasound signal U1 to the target position. Then, in Step S12, the first ultrasound signal U1 penetrates through cranial bone to reach the target position and the target position reflects the first ultrasound signal U1 to form the second ultrasound signal U2 in the estimation period. The processing device 14 drives the focused ultrasound receiver 22 to start to receive the second ultrasound signal U2 through the cranial bone only during the preset period after the estimation period. Then, in Step S14, the processing device 14 uses the display 16 to display the first image of the target position according to the second ultrasound signal U2, whereby the brightness of the first image is directly proportional to the energy intensity of the first ultrasound signal U1.

The first image is displayed according to first beamformed filtered data $\tilde{rf}(x_g, y_g, z_g)$, and the first beamformed filtered data $\tilde{rf}(x_g, y_g, z_g)$ satisfies following formulas (11), (12), (13), (14) and (15):

$$\tilde{rf}(x_g, z_g) = F \otimes \sum_{n=1}^{N}\left(\sum_{n=1}^{N}\left((\hat{RF}_{M\times N})^T \times x_{M\times 1} \times \overline{TD_{1\times N}}\right)\right) \quad (11)$$

$$\hat{RF}_{M\times N} \cong \cos(2\pi f_r t) \times \left(ch\hat{RF}_{M\times N} + ch\hat{RF}^*_{M\times N}\right)/2 - \sin(2\pi f_r t) \times (-j) \times \left(ch\hat{RF}_{M\times N} + ch\hat{RF}^*_{M\times N}\right)/2 \quad (12)$$

$$\hat{IQ}_{m\times N} \cong [f_1(k), f_2(k), \ldots, f_i(k), \ldots, f_N(k)] \quad (13)$$

$$ch\hat{RF}_{M\times N} \cong \left[f_1\left(\frac{k}{f_{sIQ}} * f_{sRF}\right), f_2\left(\frac{k}{f_{sIQ}} * f_{sRF}\right), \ldots, f_i\left(\frac{k}{f_{sIQ}} * f_{sRF}\right), \ldots, f_N\left(\frac{k}{f_{sIQ}} * f_{sRF}\right)\right] \quad (14)$$

$$T_{M\times N} = x_{M\times 1} \times \overline{TD_{1\times N}} \quad (15)$$

Wherein, $(x_g, y_g, z_g)$ is 3-D coordinate of the target position, and F is a first filtered factor, and N is an amount of the focused ultrasound receiver 22, and n is an index of each focused ultrasound receiver 22, and $\hat{RF}_{M\times N}$ is a first beamformed data matrix with dimension M×N, and t is time, and $f_r$ is a first re-modulation frequency, and $ch\hat{RF}_{M\times N}$ is a first channel data matrix with dimension M×N, and $\hat{IQ}_{M\times N}$ is a matrix with dimension m×N of a baseband signal of the second ultrasound signal U2, and m is a natural number, and $f_i(k)$ is a column function of a i-th column of $\hat{IQ}_{m\times N}$, and k and i are natural numbers, and k=1,2, . . . , m, and i=1, 2, . . . , N, and $f_{sIQ}$ is a sampling frequency of $\hat{IQ}_{m\times N}$, and $f_{sRF}$ is a resampled frequency of $\hat{IQ}_{m\times N}$, and $\overline{TD_{1\times N}}$ is a first time matrix of the second ultrasound signal U2 moving from the target position to N pieces of the focused ultrasound receivers 22, and $T_{M\times N}$ is a mask-operated matrix with dimension M×N comprising binary element 0 or 1, and M is a natural number larger than the largest element of the first time matrix, and $x_{M\times 1}$ is a vector with dimension M×1, $ch\hat{RF}_{M\times N}^*$ is a conjugation of $ch\hat{RF}_{M\times N}$, and ⊗ is convolution operation.

Like the first embodiment, the second embodiment uses the processing device 14 to set the preset brightness as an energy level intended to apply to the target position of the organism 17.

After the calibration process, an execution process is performed. The execution process comprises Step S16, Step S18 and Step S20. In the execution process, Step S16 is firstly performed. In Step S16, the processing device 14 converts the first electrical signal E1 into the second electrical signal E2 received by the focused ultrasound emitter 20 according to the difference between the brightness of the first image and the preset brightness, whereby the focused ultrasound emitter 20 uses the second electrical signal E2 to emit the third ultrasound signal U3 whose energy intensity larger than the energy intensity of the first ultrasound signal U1 to the target position. Then, in Step S18, the third ultrasound signal U3 penetrates through the cranial bone to reach the target position and the target position reflects the third ultrasound signal U3 to form the fourth ultrasound signal U4 in the estimation period. The processing device 14 drives the focused ultrasound receiver 22 to start to receive the fourth ultrasound signal U4 through the cranial bone only during the preset period after the estimation period. Then, in Step S20, the processing device 14 uses the display 16 to display the second image of the target position according to the fourth ultrasound signal U4, whereby the brightness of the second image is directly proportional to the energy intensity of the third ultrasound signal U3.

The second image is displayed according to second beamformed filtered data $\tilde{rf}(x_g, y_g, z_g)'$, and the second beamformed filtered data $\tilde{rf}(x_g, y_g, z_g)'$ satisfies following formulas (16), (17), (18), (19) and (20):

$$\tilde{rf}(x_g, y_g, z_g)' = F' \otimes \sum_{n=1}^{N}\left(\sum_{n=1}^{N}\left((\hat{RF}'_{M'\times N})^T \times x'_{M'\times 1} \times \overline{TD'_{1\times N}}\right)\right) \quad (16)$$

-continued $$\hat{RF}'_{M'\times N} \cong \cos(2\pi f'_r t) \times (ch\hat{RF}'_{M'\times N} + ch\hat{RF}'^*_{M'\times N})/2 - \sin(2\pi f'_r t) \times (-j) \times (ch\hat{RF}'_{M'\times N} + ch\hat{RF}'^*_{M'\times N})/2 \quad (17)$$

$$\hat{IQ}'_{m'\times N} \cong [f'_1(k), f'_2(k), \ldots, f'_i(k), \ldots, f'_N(k)] \quad (18)$$

$$ch\hat{RF}'_{M'\times N} \cong \left[ f'_1\left(\frac{k}{f'_{sIQ}} * f'_{sRF}\right), f'_2\left(\frac{k}{f'_{sIQ}} * f'_{sRF}\right), \ldots, f'_i\left(\frac{k}{f'_{sIQ}} * f'_{sRF}\right), \ldots, f'_N\left(\frac{k}{f'_{sIQ}} * f'_{sRF}\right) \right] \quad (19)$$

$$T'_{M'\times N} = x'_{M'\times 1} \times \overline{TD'_{1\times N}} \quad (20)$$

Wherein, $(x_g, y_g, z_g)$ is coordinates of the target position, and F' is a second filtered factor, and N is an amount of the focused ultrasound receiver 22, and n is an index of each focused ultrasound receiver 22, and $\hat{RF}'_{M'\times N}$ is a second beamformed data matrix with dimension M'×N, and t is time, and $f'_r$ is a second re-modulation frequency, and $ch\hat{RF}'_{M'\times N}$ is a second channel data matrix with dimension M'×N, and $\hat{IQ}'_{m\times N}$ is a matrix with dimension m×N of a baseband signal of the fourth ultrasound signal U4, and in is a natural number, and $f'_i(k)$ is a column function of a i-th column of $\hat{IQ}'_{m\times N}$, and k and i are natural numbers, and k=1,2, . . . , m, and i=1,2, . . . , N, and $f_{sIQ}'$ is a sampling frequency of $\hat{IQ}'_{m\times N}$, and $f_{sRF}'$ is a resampled frequency of $\hat{IQ}'_{m\times N}$, and $\overline{TD'_{1\times N}}$ is a second time matrix of the fourth ultrasound signal U4 moving from the target position to N pieces of the focused ultrasound receivers 22, and $T'_{M\times N}$ is a mask-operated matrix with dimension M'×N comprising binary element 0 or 1, and M' is a natural number larger than the largest element of the second time matrix, and $x'_{M'\times 1}$ is a vector with dimension M'×1, and $ch\hat{RF}'_{M'\times N}*$ is a conjugation of $ch\hat{RF}'_{M'\times N}$, and ⊗ is convolution operation.

After Step S20, the operation process returns to Step S10 to sequentially perform the calibration process and the execution process on another target position. Repeatedly, an activity of applying energy to a therapy region of the BBB is also completed to achieve the purpose of opening the BBB in CNS tissue and delivering drugs.

Besides, before the calibration process, the processing device 14 generates an electrical signal and transmits the electrical signal to the focused ultrasound emitter 20 to control the focused ultrasound emitter 20 to emit an ultrasound signal to a calibrated tool such as a force balanced meter or a calibrated hydrophone for acoustic power measurement, whereby the correlation between level of ultrasound signal and the level of emitted energy can be established after performing the calibration process.

Figure 7A:
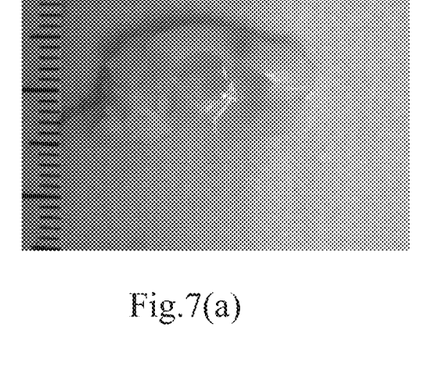
Figure 7B:
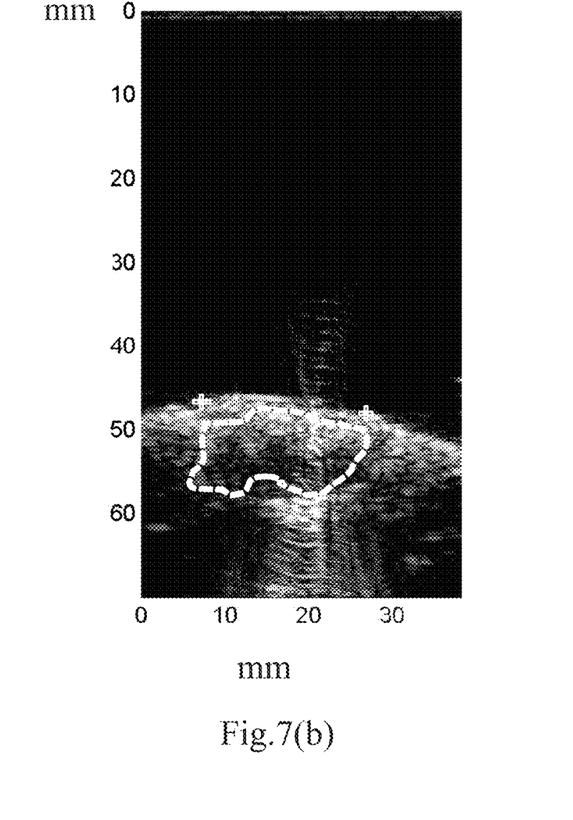
Figure 8A:
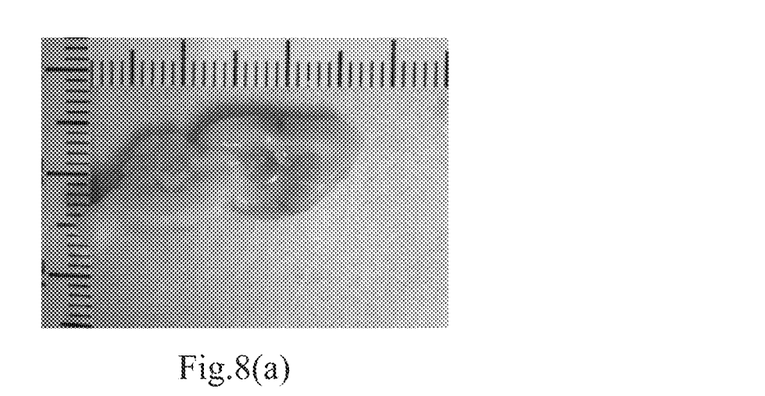
Figure 8B:
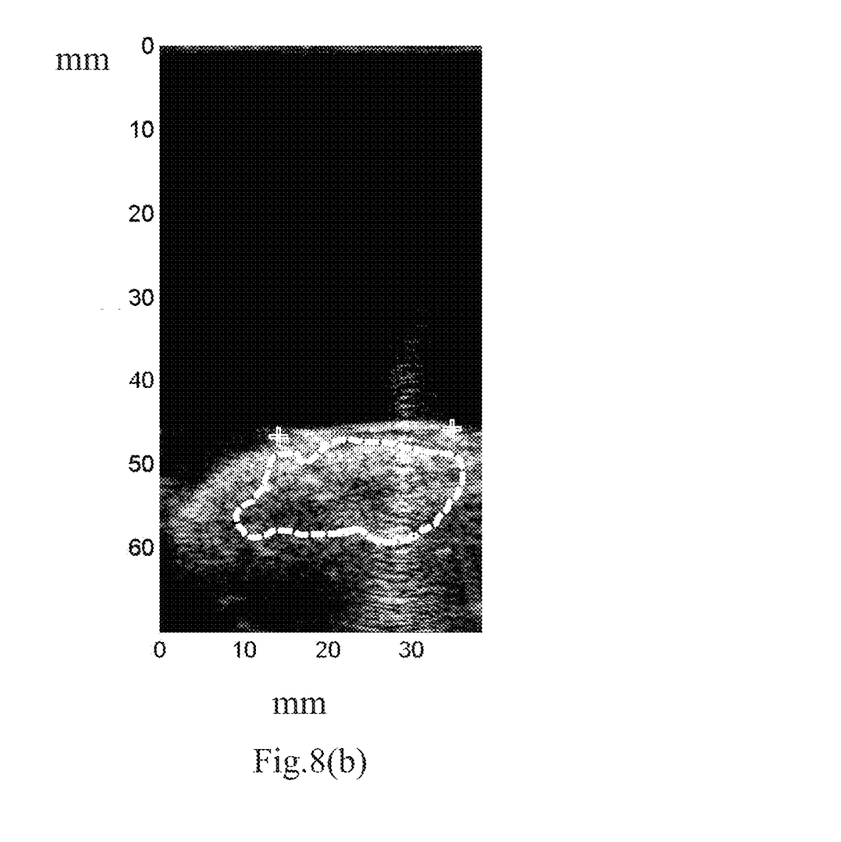
Figure 9:
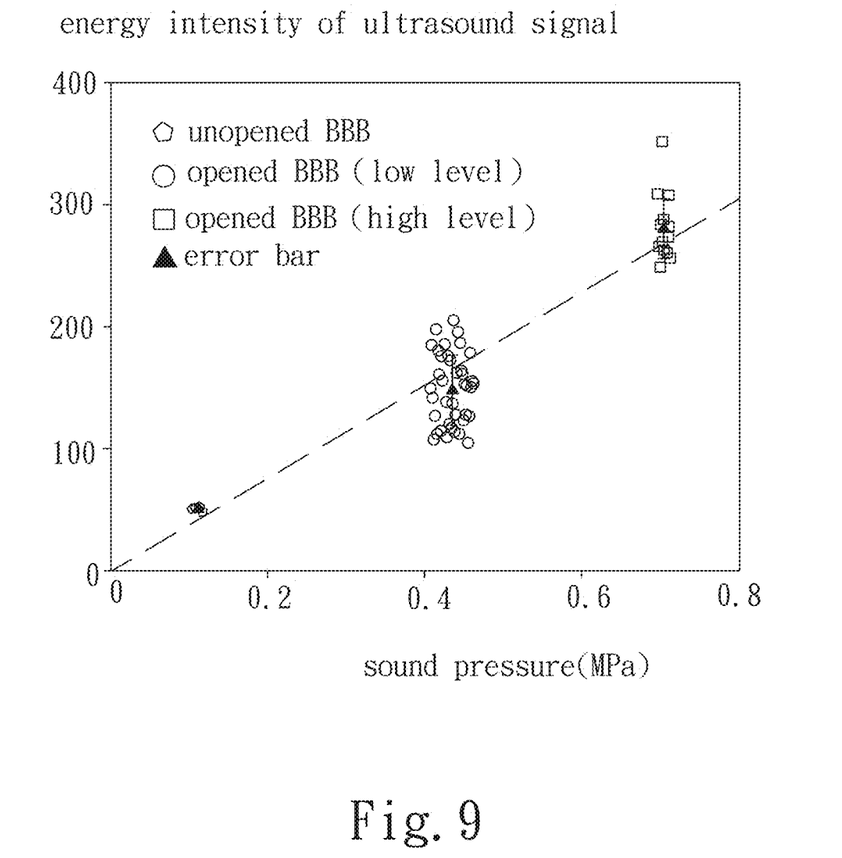
FIG. 9 is a diagram showing proportional relationship between energy intensity of an ultrasound signal and sound pressure according to an embodiment of the present invention.

The suitable ultrasound energy intensity can open the BBB at the targeted focused region without damaging the CNS capillary structure. In that circumstances, the stronger the energy intensity of ultrasound applied to the CNS target is, the more BBB opens and the higher the brightness of the second image is. Refer to FIG. 7(a) and FIG. 7(b) which are respectively a diagram of an image of CNS tissue under sound pressure of 0.467 MPa and a diagram of the second image corresponded thereof, wherein the input power of the third ultrasound signal is 4.54 W. From the figures, it is known that the ultrasound energy applies to the position of the CNS tissue having deeper color and the second image corresponding to the deeper color position has higher brightness. Refer to FIG. 8(a) and FIG. 8(b) which are respectively a diagram of an image of BBB under sound pressure of 0.705 MPa and a diagram of the second image corresponded thereof, wherein the energy of the third input electrical power is 9.12 W. From the figures, it is known that the ultrasound energy applies to the position of the BBB having deeper color and the second image corresponding to the deeper color position has higher brightness. Compared with FIG. 7(b), FIG. 8(b) has higher brightness. This is because the energy intensity of the third ultrasound signal increases. In addition, FIG. 9 is a diagram showing proportional relationship between energy intensity of the emitted ultrasound signal and the sound pressure applied to BBB, wherein a pentagon denotes unopened BBB, a circle denotes opened BBB with low level, a quadrilateral denotes opened BBB with high level, and a triangle denotes an error bar of the three abovementioned data. From FIG. 9, it is known that the energy intensity of the emitted ultrasound signal is directly proportional to the sound pressure applied to the targeted CNS tissue and cause various level of BBB opening, as shown by a dash line.

In conclusion, the present invention emits an ultrasound signal to an targeted CNS organism. Then, after an estimation period, the present invention starts to receive the backscattering ultrasound signal, thereby generating an image of the targeted CNS organism. Wherein, brightness of the image is directly proportional to energy intensity of the ultrasound signal to know how much energy applied to the organism and achieve the purpose of opening the BBB and delivering drugs.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A display device for ultrasound energy comprising:
    a focused ultrasound emitting and receiving device configured to emit at least one first ultrasound signal to a target position of an organism, and said target position reflects said first ultrasound signal to form at least one second ultrasound signal;
    a processing device comprising a hardware, connected with said focused ultrasound emitting and receiving device and configured to set an estimation period according to a distance between said focused ultrasound emitting and receiving device and said target position and sound-traveling speed, said processing device is configured to generate a first electrical signal and transmit said first electrical signal to said focused ultrasound emitting and receiving device to control said focused ultrasound emitting and receiving device to emit said first ultrasound signal, said processing device drives said focused ultrasound emitting and receiving device to start to receive said second ultrasound signal only during a preset period after said estimation period, and said preset period is equal to or larger than response time of said focused ultrasound emitting and receiving device; and
    a display connected with said processing device, said processing device is configured to use said display to display a first image of said target position according to said second ultrasound signal, brightness of said first image is directly proportional to energy intensity of said first ultrasound signal, said focused ultrasound emitting and receiving device further comprises a plurality of focused ultrasound transducers configured to receive said first electrical signal to generate said first ultrasound signal according to said first electrical signal, said processing device is configured to drive said plurality of focused ultrasound transducers to receive said second ultrasound signal, said preset period is equal to or larger than response time of said plurality of focused ultrasound transducers, said first image is displayed according to first beamformed filtered data $\tilde{rf}(x_g,y_g,z_g)$, and said first beamformed filtered data $\tilde{rf}(x_g,y_g,z_g)$ satisfies following formulas:

$$\tilde{rf}(x_g, y_g, z_g) = F \otimes \sum_{n=1}^{N}\left(\sum_{n=1}^{N}\left((\hat{RF}_{M\times N})^T \times x_{M\times 1} \times \overline{TD_{1\times N}}\right)\right);$$

$$\hat{RF}_{M\times N} \cong \cos(2\pi f_r t) \times (ch\hat{RF}_{M\times N} + ch\hat{RF}^*_{M\times N})/2 -$$
$$\sin(2\pi f_r t) \times (-j) \times (ch\hat{RF}_{M\times N} + ch\hat{RF}^*_{M\times N})/2;$$

$$\hat{IQ}_{m\times N} \cong [f_1(k), f_2(k), \ldots, f_i(k), \ldots, f_N(k)];$$

$$ch\hat{RF}_{M\times N} \cong \left[f_1\left(\frac{k}{f_{sIQ}} * f_{sRF}\right), f_2\left(\frac{k}{f_{sIQ}} * f_{sRF}\right), \ldots, \right.$$
$$\left. f_i\left(\frac{k}{f_{sIQ}} * f_{sRF}\right), \ldots, f_N\left(\frac{k}{f_{sIQ}} * f_{sRF}\right)\right];$$

and $$T_{M\times N} = x_{M-1} \times \overline{TD_{1\times N}},$$

wherein ($x_g$, $y_g$, $z_g$) is 3-D coordinate of said target position, F is a first filtered factor, N is number of said plurality of focused ultrasound transducers, n is an index of each of said plurality of focused ultrasound transducers, $\hat{RF}_{M\times N}$ is a first beamformed data matrix with dimension M×N, t is time, $f_r$ is a first re-modulation frequency, $ch\hat{RF}_{M\times N}$ is a first channel data matrix with dimension M×N, $\hat{IQ}_{m\times N}$ is a matrix with dimension m×N of a baseband signal of said second ultrasound signal, m is a natural number, $f_i(k)$ is a column function of a i-th column of $\hat{IQ}_{m\times N}$, k and i are natural numbers, k=1,2,...,m, i=1,2,...,N, $f_{sIQ}$ is a sampling frequency of $\hat{IQ}_{m\times N}$, $f_{sRF}$ is a resampled frequency of $\hat{IQ}_{m\times N}$, $\overline{TD_{1\times N}}$ is a first time matrix of said second ultrasound signal moving from said target position to N pieces of said plurality of focused ultrasound transducers, $T_{M\times N}$ is a mask-operated matrix with dimension M×N comprising binary element 0 or 1, M is a natural number larger than a largest element of said first time matrix, $x_{M\times 1}$ is a vector with dimension M×1, $ch\hat{RF}_{M\times N}^*$ is a conjugation of $ch\hat{RF}_{M\times N}$, said plurality of focused ultrasound transducers are different distances from the target position, a corresponding focused ultrasound transducer of said plurality of focused ultrasound transducers is distal from said target position, and said estimation period equals a distance between said target position and said corresponding focused ultrasound transducer multiplied by 2 and divided by said sound-traveling speed.

2. The display device for ultrasound energy according to claim 1, wherein said plurality of focused ultrasound transducers are arranged into a two-dimension array or a concentric circle array.

3. The display device for ultrasound energy according to claim 1, wherein said organism is a central nervous system (CNS) tissue having capillaries containing blood-brain barrier.

4. A display device for ultrasound energy comprising:
a focused ultrasound emitting and receiving device configured to emit at least one first ultrasound signal to a target position of an organism, and said target position reflects said first ultrasound signal to form at least one second ultrasound signal;

a processing device comprising hardware, connected with said focused ultrasound emitting and receiving device and configured to set an estimation period according to a distance between said focused ultrasound emitting and receiving device and said target position and sound-traveling speed, said processing device is configured to generate a first electrical signal and transmits said first electrical signal to said focused ultrasound emitting and receiving device to control said focused ultrasound emitting and receiving device to emit said first ultrasound signal, then said processing device drives said focused ultrasound emitting and receiving device to start to receive said second ultrasound signal only during a preset period after said estimation period, and said preset period is equal to or larger than response time of said focused ultrasound emitting and receiving device; and a display connected with said processing device, said processing device is configured to uses said display to display a first image of said target position according to said second ultrasound signal, brightness of said first image is directly proportional to energy intensity of said first ultrasound signal, said focused ultrasound emitting and receiving device further comprises a plurality of focused ultrasound transducers configured to receive said first electrical signal to generate said first ultrasound signal according to said first electrical signal, said processing device is configured to drive said plurality of focused ultrasound transducers to receive said second ultrasound signal, said preset period is equal to or larger than response time of said plurality of focused ultrasound transducers, said processing device is configured to convert said first electrical signal into a second electrical signal according to a difference between said brightness of said first image and preset brightness, each of said plurality of focused ultrasound transducers is configured to receive said second electrical signal and use said second electrical signal to emit at least one third ultrasound signal whose energy intensity larger than energy intensity of said first ultrasound signal to said target position, said target position reflects said third ultrasound signal to form at least one fourth ultrasound signal, after generating said third ultrasound signal, said processing device drives each of said plurality of focused ultrasound transducers to start to receive said fourth ultrasound signal only during said preset period after said estimation period, said processing device is configured to use said display to display a second image of said target position according to said fourth ultrasound signal, and brightness of said second image is directly proportional to energy intensity of said third ultrasound signal.

5. The display device for ultrasound energy according to claim 4, wherein said second image is displayed according to second beamformed filtered data $\tilde{rf}(x_g,y_g,z_g)'$, and said second beamformed filtered data $\tilde{rf}(x_g,y_g,z_g)'$ satisfies following formulas:

$$\tilde{rf}(x_g, y_g, z_g)' = F' \otimes \sum_{n=1}^{N}\left(\sum_{n=1}^{N}\left((\hat{RF}'_{M'\times N})^T \times x'_{M'\times 1} \times \overline{TD'_{1\times N}}\right)\right);$$

-continued $$\hat{RF}'_{M'\times N} \cong \cos(2\pi f'_r t) \times (ch\hat{RF}'_{M'\times N} + ch\hat{RF}'^{*}_{M'\times N})/2 -$$
$$\sin(2\pi f'_r t) \times (-j) \times (ch\hat{RF}'_{M'\times N} + ch\hat{RF}'^{*}_{M'\times N})/2;$$

$$\hat{IQ}'_{m'\times N} \cong [f'_1(k), f'_2(k), \ldots, f'_i(k), \ldots, f'_N(k)];$$

$$ch\hat{RF}'_{M'\times N} \cong \left[ f'_1\left(\frac{k}{f'_{sIQ}} * f'_{sRF}\right), f'_2\left(\frac{k}{f'_{sIQ}} * f'_{sRF}\right), \ldots, \right.$$
$$\left. f'_i\left(\frac{k}{f'_{sIQ}} * f'_{sRF}\right), \ldots, f'_N\left(\frac{k}{f'_{sIQ}} * f'_{sRF}\right) \right];$$

and $$T'_{M'\times N} = x'_{M'\times 1} \times \overline{TD'_{1\times N}},$$

wherein $(x_g, Y_g, Z_g)$ is 3-D coordinate of said target position, F' is a second filtered factor, N is number of said plurality of focused ultrasound transducers, n is an index of each of said plurality of focused ultrasound transducers, $\hat{RF}'_{M'\times N}$ is a second beamformed data matrix with dimension M'×N, t is time, $f'_r$ is a second re-modulation frequency, $ch\hat{RF}'_{M'\times N}$ is a second channel data matrix with dimension M'×N, $\hat{IQ}'_{m\times N}$ is a matrix with dimension m×N of a baseband signal of said fourth ultrasound signal, m is a natural number, $f'_i(k)$ is a column function of a i-th column of $\hat{IQ}'_{m\times N}$, k and i are natural numbers, k=1,2, . . . , m, i=1,2, . . . , N, $f_{sIQ}'$ is a sampling frequency of $\hat{IQ}'_{m\times N}$, $f_{sRF}'$ is a resampled frequency of $\hat{IQ}'_{m\times N}$, $\overline{TD'_{1\times N}}$ is a second time matrix of said fourth ultrasound signal moving from said target position to N pieces of said plurality of focused ultrasound transducers, $T'_{M\times N}$ is a matrix with dimension M'×N comprising binary element 0 or 1, M' is a natural number larger than a largest element of said second time matrix, $x'_{M'\times 1}$ is a vector with dimension M'×1, $ch\hat{RF}'_{M'\times N}{}^*$ is a conjugation of $ch\hat{RF}'_{M'\times N}$, $\otimes$ is convolution operation, said plurality of focused ultrasound transducers are different distances from the target position, a corresponding focused ultrasound transducer of said plurality of focused ultrasound transducers is distal from said target position, and said estimation period equals a distance between said target position and said corresponding focused ultrasound transducer multiplied by 2 and divided by said sound-traveling speed.

6. The display device for ultrasound energy according to claim 4, wherein said third ultrasound signal and said fourth ultrasound signal are burst waves.

7. The display device for ultrasound energy according to claim 6, wherein said first ultrasound signal and said second ultrasound signal are burst waves.

8. The display device for ultrasound energy according to claim 6, wherein said first ultrasound signal and said third ultrasound signal penetrate through cranial bone to reach said target position, and frequency of said first ultrasound signal and said third ultrasound signal is inversely proportional to thickness of said cranial bone.

9. A display device for ultrasound energy comprising:
a focused ultrasound emitting and receiving device configured to emit at least one first ultrasound signal to a target position of an organism, and said target position reflects said first ultrasound signal to form at least one second ultrasound signal;
a processing device comprising hardware, connected with said focused ultrasound emitting and receiving device and configured to set an estimation period according to a distance between said focused ultrasound emitting and receiving device and said target position and sound-traveling speed, said processing device is configured to generate a first electrical signal and transmit said first electrical signal to said focused ultrasound emitting and receiving device to control said focused ultrasound emitting and receiving device to emit said first ultrasound signal, said processing device drives said focused ultrasound emitting and receiving device to start to receive said second ultrasound signal only during a preset period after said estimation period, and said preset period is equal to or larger than response time of said focused ultrasound emitting and receiving device; and
a display connected with said processing device, said processing device is configured to use said display to display a first image of said target position according to said second ultrasound signal, brightness of said first image is directly proportional to energy intensity of said first ultrasound signal, said focused ultrasound emitting and receiving device further comprises at least one focused ultrasound emitter and at least one focused ultrasound receiver connected with said processing device, said at least one focused ultrasound emitter is surrounded by said at least one focused ultrasound receiver, or vice versa, said at least one focused ultrasound emitter is configured to receive said first electrical signal and generate said first ultrasound signal according to said first electrical signal, said processing device drives said at least one focused ultrasound receiver to receive said second ultrasound signal, said preset period is equal to or larger than response time of said at least one focused ultrasound receiver, said first image is displayed according to first beamformed filtered data $\tilde{rf}(x_g,y_g,z_g)$, and said first beamformed filtered data $\tilde{rf}(x_g,y_g, z_g)$ satisfies following formulas:

$$\tilde{rf}(x_g, y_g, z_g) = F \otimes \sum_{n=1}^{N}\left(\sum_{n=1}^{N}\left((\hat{RF}_{M\times N})^T \times x_{M\times 1} \times \overline{TD_{1\times N}}\right)\right);$$

$$\hat{RF}_{M\times N} \cong \cos(2\pi f_r t) \times (ch\hat{RF}_{M\times N} + ch\hat{RF}^{*}_{M\times N})/2 -$$
$$\sin(2\pi f_r t) \times (-j) \times (ch\hat{RF}_{M\times N} + ch\hat{RF}^{*}_{M\times N})/2;$$

$$\hat{IQ}_{m\times N} \cong [f_1(k), f_2(k), \ldots, f_i(k), \ldots, f_N(k)];$$

$$ch\hat{RF}_{M\times N} \cong \left[ f_1\left(\frac{k}{f_{sIQ}} * f_{sRF}\right), f_2\left(\frac{k}{f_{sIQ}} * f_{sRF}\right), \ldots, \right.$$
$$\left. f_i\left(\frac{k}{f_{sIQ}} * f_{sRF}\right), \ldots, f_N\left(\frac{k}{f_{sIQ}} * f_{sRF}\right) \right];$$

and $$T_{M\times N} = x_{M-1} \times \overline{TD_{1\times N}},$$

wherein $(x_g, y_g, z_g)$ is 3-D coordinate of said target position, F is a first filtered factor, N is number of said at least one focused ultrasound receiver, n is an index of said at least one focused ultrasound receiver, $\hat{RF}_{M\times N}$ is a first beamformed data matrix with dimension M×N, t is time, $f_r$ is a first re-modulation frequency, $ch\hat{RF}_{M\times N}$ is a first channel data matrix with dimension M×N, $\hat{IQ}_{m\times N}$ is a matrix with dimension m×N of a baseband signal of said second ultrasound signal, m is a natural number, $f_i(k)$ is a column function of a i-th column of $\hat{IQ}_{m\times N}$, k and i are natural numbers, k=1,2, . . . , m, i=1,2, . . . , N, $f_{sIQ}$ is a sampling frequency of $\hat{IQ}_{m\times N}$, $f_{sRF}$ is a resampled frequency of $\hat{IQ}_{m\times N}$, $\overline{TD_{1\times N}}$ is a first time matrix of said second ultrasound signal moving from said target position to said at least one focused ultrasound receivers, $T_{M\times N}$ is a mask-operated matrix with dimension M×N comprising binary elements 0 or 1, M is a natural number larger than a largest element of said first time matrix, $x_{M \times 1}$ is a vector with dimension M×1, $ch\hat{RF}_{M \times N}{}^*$ is a conjugation of $ch\hat{RF}_{M \times N}$, $\otimes$ is convolution operation, and said estimation period equals a distance between said target position and said at least one focused ultrasound receiver multiplied by 2 and divided by said sound-traveling speed.

10. The display device for ultrasound energy according to claim 9, wherein said at least one focused ultrasound receiver further comprises a plurality of focused ultrasound receivers arranged into a strip array with one dimension, and said plurality of focused ultrasound receivers and said at least one focused ultrasound emitter are arranged on a curved surface.

11. The display device for ultrasound energy according to claim 9, wherein said at least one focused ultrasound receiver further comprises a plurality of focused ultrasound receivers arranged into a ring array, and said plurality of focused ultrasound receivers and at least one said focused ultrasound emitter are arranged on a curved surface.

12. A display device for ultrasound energy comprising:
a focused ultrasound emitting and receiving device configured to emit at least one first ultrasound signal to a target position of an organism, and said target position reflects said first ultrasound signal to form at least one second ultrasound signal;
a processing device comprising hardware, connected with said focused ultrasound emitting and receiving device and configured to set an estimation period according to a distance between said focused ultrasound emitting and receiving device and said target position and sound-traveling speed, said processing device is configured to generates a first electrical signal and transmits said first electrical signal to said focused ultrasound emitting and receiving device to control said focused ultrasound emitting and receiving device to emit said first ultrasound signal, then said processing device drives said focused ultrasound emitting and receiving device to start to receive said second ultrasound signal only during a preset period after said estimation period, and said preset period is equal to or larger than response time of said focused ultrasound emitting and receiving device; and
a display connected with said processing device, said processing device is configured to uses said display to display a first image of said target position according to said second ultrasound signal, brightness of said first image is directly proportional to energy intensity of said first ultrasound signal, said focused ultrasound emitting and receiving device further comprises at least one focused ultrasound emitter and at least one focused ultrasound receiver connected with said processing device, said at least one focused ultrasound emitter is surrounded by said at least one focused ultrasound receiver, or vice versa, said at least one focused ultrasound emitter is configured to receive said first electrical signal and generate said first ultrasound signal according to said first electrical signal, said processing device drives said at least one focused ultrasound receiver to receive said second ultrasound signal, said preset period is equal to or larger than response time of said at least one focused ultrasound receiver, said processing device is configured to convert said first electrical signal into a second electrical signal according to a difference between said brightness of said first image and preset brightness, said at least one focused ultrasound receiver is configured to receive said second electrical signal, said at least one focused ultrasound emitter is configured to use said second electrical signal to emit at least one third ultrasound signal whose energy intensity larger than energy intensity of said first ultrasound signal to said target position, said target position reflects said third ultrasound signal to form at least one fourth ultrasound signal, after generating said third ultrasound signal, said processing device drives said at least one focused ultrasound receiver to start to receive said fourth ultrasound signal only during said preset period after said estimation period, said processing device is configured to use said display to display a second image of said target position according to said fourth ultrasound signal, and brightness of said second image is directly proportional to energy intensity of said third ultrasound signal.

13. The display device for ultrasound energy according to claim 12, wherein said second image is displayed according to second beamformed filtered data $\tilde{rf}(x_g, y_g, z_g)'$, and said second beamformed filtered data $\tilde{rf}(x_g, y_g, z_g)'$ satisfies following formulas:

$$\tilde{rf}(x_g, y_g, z_g)' = F' \otimes \sum_{n=1}^{N} \left( \sum_{n=1}^{N} \left( (\hat{RF}'_{M' \times N})^T \times x'_{M' \times 1} \times \overline{TD'_{1 \times N}} \right) \right);$$

$$\hat{RF}'_{M' \times N} \cong \cos(2\pi f'_r t) \times (ch\hat{RF}'_{M' \times N} + ch\hat{RF}'^*_{M' \times N})/2 -$$
$$\sin(2\pi f'_r t) \times (-j) \times (ch\hat{RF}'_{M' \times N} + ch\hat{RF}'^*_{M' \times N})/2;$$

$$\hat{IQ}'_{m' \times N} \cong [f'_1(k), f'_2(k), \ldots, f'_i(k), \ldots, f'_N(k)];$$

$$ch\hat{RF}'_{M' \times N} \cong \left[ f'_1\left(\frac{k}{f'_{sIQ}} * f'_{sRF}\right), f'_2\left(\frac{k}{f'_{sIQ}} * f'_{sRF}\right), \ldots, \right.$$
$$\left. f'_i\left(\frac{k}{f'_{sIQ}} * f'_{sRF}\right), \ldots, f'_N\left(\frac{k}{f'_{sIQ}} * f'_{sRF}\right) \right];$$

and $$T'_{M' \times N} = x'_{M' \times 1} \times \overline{TD'_{1 \times N}},$$

wherein $(x_g, y_g, z_g)$ is 3-D coordinate of said target position, F' is a second filtered factor, N is number of said at least one focused ultrasound receiver, n is an index of said at least one focused ultrasound receiver, $\hat{RF}'_{M' \times N}$ is a second beamformed data matrix with dimension M'×N, t is time, $f_r'$ is a second re-modulation frequency, $ch\hat{RF}'_{M' \times N}$ is a second channel data matrix with dimension M'×N, $\hat{IQ}'_{m \times N}$ is a matrix with dimension m×N of a baseband signal of said fourth ultrasound signal, m is a natural number, $f_i'(k)$ is a column function of a i-th column of $\hat{IQ}'_{m \times N}$, k and i are natural numbers, k=1,2, ..., m, i=1,2, ..., N, $f_{sIQ}$ is a sampling frequency of $\hat{IQ}'_{m \times N}$, $f_{sRF}'$ is a resampled frequency of $\hat{IQ}'_{m \times N}$, $\overline{TD'_{1 \times N}}$ is a second time matrix of said fourth ultrasound signal moving from said target position to said at least one focused ultrasound receiver, $T'_{M \times N}$ is a matrix with dimension M'×N comprising binary element 0 or 1, M' is a natural number larger than a largest element of said second time matrix, $x'_{M' \times 1}$ is a vector with dimension M'×1, $ch\hat{RF}'_{M' \times N}{}^*$ is a conjugation of $ch\hat{RF}'_{M' \times N}$, $\otimes$ is convolution operation, and said estimation period equals a distance between said target position and said at least one focused ultrasound receiver multiplied by 2 and divided by said sound-traveling speed.

14. The display device for ultrasound energy according to claim 12, wherein said at least one focused ultrasound receiver further comprises a plurality of focused ultrasound receivers arranged into a strip array with one dimension, and said plurality of focused ultrasound receivers and said at least one focused ultrasound emitter are arranged on a curved surface.

15. The display device for ultrasound energy according to claim 12, wherein said at least one focused ultrasound receiver further comprises a plurality of focused ultrasound receivers arranged into a ring array, and said plurality of focused ultrasound receivers and at least one said focused ultrasound emitter are arranged on a curved surface.

16. The display device for ultrasound energy according to claim 12, wherein said third ultrasound signal and said fourth ultrasound signal are burst waves.

17. The display device for ultrasound energy according to claim 16, wherein said first ultrasound signal and said second ultrasound signal are burst waves.

18. The display device for ultrasound energy according to claim 16, wherein said first ultrasound signal and said third ultrasound signal penetrate through cranial bone to reach said target position, and frequency of said first ultrasound signal and said third ultrasound signal is inversely proportional to thickness of said cranial bone.

* * * * *